United States Patent [19]

Rowsey, Jr.

[11] Patent Number: 5,988,824
[45] Date of Patent: Nov. 23, 1999

[54] ANTERIOR SEGMENT MIRROR AND METHOD OF USE FOR CORNEAL TRANSPLANT SURGERY

[75] Inventor: John James Rowsey, Jr., Tampa, Fla.

[73] Assignee: University of South Florida, Tampa, Fla.

[21] Appl. No.: 08/856,134

[22] Filed: May 14, 1997

Related U.S. Application Data

[60] Provisional application No. 60/017,596, May 14, 1996.

[51] Int. Cl.$^6$ ............................ G02B 7/182; A61B 17/00
[52] U.S. Cl. ......................... 359/882; 359/871; 359/900; 600/247; 606/4; 606/18; 606/139; 606/147; 128/898
[58] Field of Search ..................................... 359/871, 882, 359/900; 606/4, 18, 139, 147; 128/898; 600/247

[56] References Cited

U.S. PATENT DOCUMENTS

| 539,076 | 5/1895 | McNaughton | 600/247 |
| 727,483 | 5/1903 | Street | 600/247 |
| 3,120,847 | 2/1964 | Cavaness | 606/147 |
| 4,512,635 | 4/1985 | Melde | 359/882 |
| 5,665,069 | 9/1997 | Cumer et al. | 604/116 |

*Primary Examiner*—Ricky D. Shafer
*Attorney, Agent, or Firm*—Calfee, Halter & Griswold, LLP

[57] ABSTRACT

A mirror for use during eye surgery comprises a handle, a reflective surface oriented at a skewed angle with respect to the handle and a needle holder oriented with respect to the reflective surface to allow viewing of the distal end of the needle as it is passed under the iris and inserted into the tissue of a patient's eye.

18 Claims, 1 Drawing Sheet

ANTERIOR SEGMENT MIRROR AND METHOD OF USE FOR CORNEAL TRANSPLANT SURGERY

This application claims the benefit of U.S. Provisional Application No. 60/017,596 filed Apr. 14, 1996.

TECHNICAL FIELD

The present invention relates to a new and useful anterior segment mirror and to a method of its use for corneal transplant surgery.

INTRODUCTION

During corneal transplant surgery, involving penetrating keratoplasty with a secondary intraocular lens implantation, transcleral fixation of a posterior chamber intraocular lens (PC-IOL) offers an excellent means of visual rehabilitation especially in the absence of a supportive capsular bag. However, the standard technique of the transclerally sutured in PC-IOL is performed without view of the loops placement into the ciliary sulcus. The best estimation of the location of the ciliary sulcus has been reported (see Attachment 1) but still relies on no direct view of the needle passage underneath the iris.

SUMMARY OF THE PRESENT INVENTION

The present invention provides an anterior segment mirror which is useful for anterior segment reconstruction, and which has been modified to be further useful as a needle holder to aid in direct view of the placement of the needle for the transclerally sutured in PC-IOL.

DETAILED DESCRIPTION OF THE PREFERRED EMBODIMENT

Figure 1:
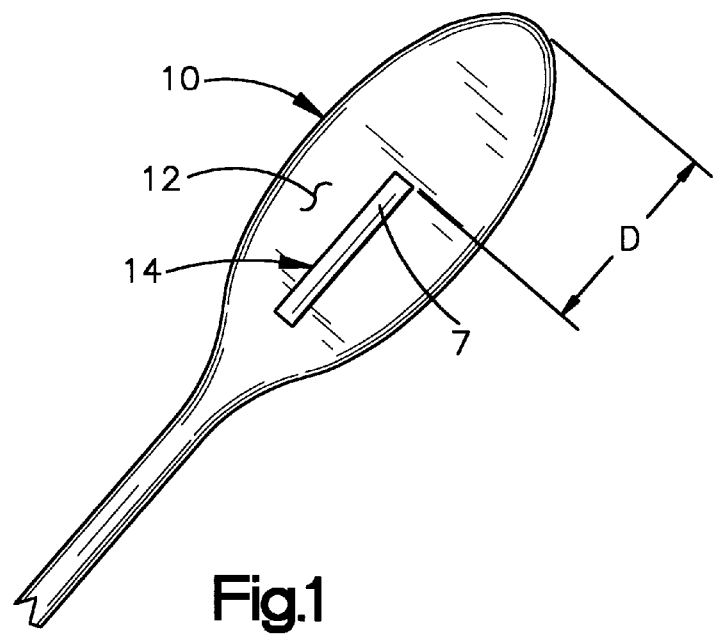
FIG. 1 is a schematic top view of an anterior segment mirror, modified to provide a needle holder according to the principles of the present invention.
Figure 2:
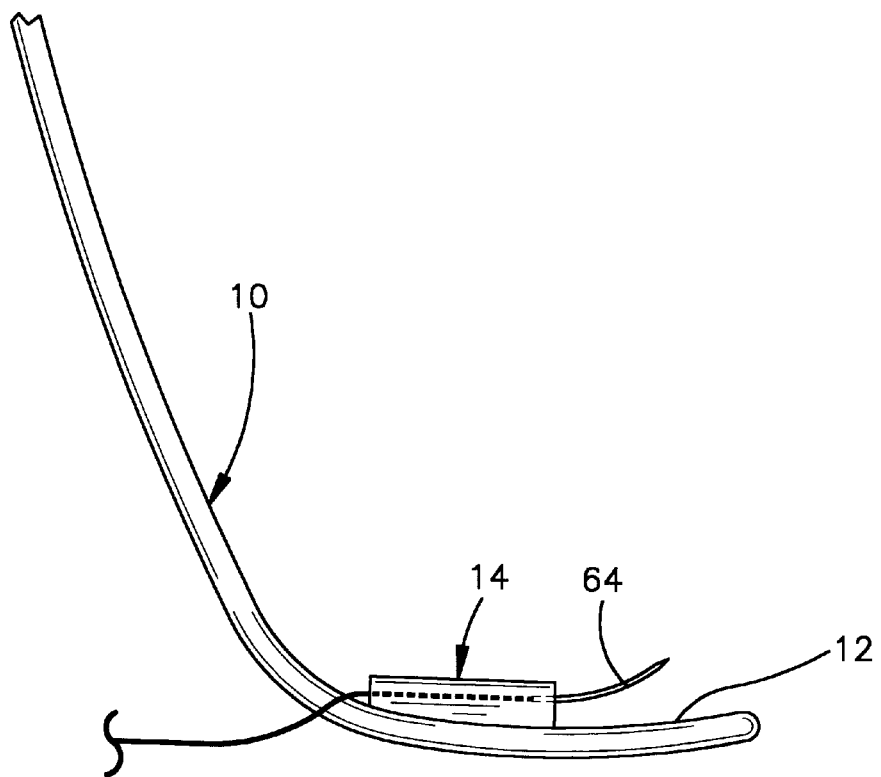
FIG. 2 is a schematic side view of the modified anterior segment mirror of FIG. 1.

FIGS. 1 and 2 schematically illustrate an anterior segment mirror 10, according to the principles of the present invention, and adapted to provide a needle holder. The anterior segment mirror 10 can be of a type available from Storz of St. Louis, Mo. The anterior segment mirror 10 is made out of titanium and its surface 12 is highly polished and smooth to give a highly reflective view.

According to the invention, the mirror has a 2.66 mm piece of 21 gauge cannula 14 attached to the surface 12, preferably by welding or soldering. The cannula 14 is made of a material such as Healon (manufactured by Ciba) or Biolon (manufactured by Pharmacia of Finland). The cannula 14 is used as a needle holder for passage of a 10-0 prolene such as Alcon AU-5 or CU-5 needle (manufactured by Aclon of Fort Worth, Tex. or Ethicon CS-160-6 needle (manufactured by Ethicon of Sommerville, N.J.) attached to a PC-IOL. The inside and the ends of the cannula 14 need to be highly polished and smooth. Also, as seen in FIG. 1, the distance D from the top of the mirror to the tip T of the cannula 14 is 3.0 mm.

To demonstrate the present invention, two fresh human postmortem eyes were used. The eyes were marked at the 12 o'clock position for orientation. The corneal buttons (7.5 mm in size) were removed. The irises were dilated by placing four sphincterotomies at the pupil border and using a Weck cell, the pupils were enlarged. The lenses and capsules were entirely removed. A meticulous anterior vitrectomy was performed underneath the iris.

The needle from the 10-0 prolene was inserted into the cannula on the anterior segment mirror and under direct view of the ciliary sulcus and the ciliary processes, the needle was passed through the sclera. This was accomplished by viewing the reflected image of the needle in the mirror to visualize the passage of the needle into the ciliary sulcus. Three passes were made in on one side of each eye. Then using calipers, preplaced marks at 0.80 mm posterior to the surgical limbus (defined by Duffey, et al., Attachment 1, as the location where the white sclera meets the blue gray zone at the limbus) in the vertical meridian and 0.45–0.50 mm in the horizontal meridian. A 9-0 or 10-0 prolene was passed underneath the iris without view and exiting at the preplace marks. Three passed were made in each eye. The eyes were fixed in 10% formalin overnight and then sectioned horizontally across the equator. The locations of the suture or needle in relationship to the ciliary sulcus and the ciliary processes were examined.

Results

A total of six passes with the two techniques were performed. On gross microscopic view, four out of the six passes with the mirror were in the ciliary sulcus. The other two were within the anterior ⅓ of the ciliary processes. With the no view technique, three out of the six were in the ciliary sulcus and two were within the anterior ciliary processes.

Discussion

The standard technique of transclerally fixated PC-IOL during secondary lens implantation relies on passage of the needle underneath the iris without view. Complications arising from poor fixation of the PC-IOL have been reported to include lens tilt, uveitis from IOL rub, perforation of the ciliary processes, hemorrhage, retinal detachment and post-op astigmatism. Duffey, et al. (Attachment 1) estimated the location of the ciliary sulcus to lie 0.46+/–0.1 mm posterior to the posterior surgical limbus in the horizontal meridian and 0.83+/–0.1 mm in the vertical meridian. This is the closest anatomic estimation of the correct placement of the PC-IOL. However, in cases of anterior rotated ciliary processes, these measurements may not be accurate. The view offered by the modified anterior segment mirror can aid in direct needle passage into the ciliary sulcus.

According to the present invention, an anterior segment mirror has been modified to be used as a needle holder. A 10-0 prolene with its needle attached to the mirror can be passed underneath the iris in a human postmortem eye. The reflection of the tip of the needle in the surface of the mirror can be seen so that once the ciliary sulcus is viewed with the mirror, the needle can be seen to enter the sulcus. This technique will require some practice with the use of the mirror, requires a good vitrectomy underneath the iris in order not to engage the needle in vitreous, and often requires a light pipe for transillumination through the scleral in order to see the sulcus, and in darkly pigmented eyes, the ciliary sulcus may still be difficult to view even with transillumination.

In summary, the present invention provides a new instrument and a new technique to fixate a PC-IOL during secondary implantation and penetrating keratoplasty. The technique uses direct visualization of the ciliary sulcus during passage of the needle underneath the iris. This technique should avoid the complications associated with the standard method of sutured in PC-IOL.

I claim:

1. A mirror for use during eye surgery, comprising:
   a. a handle;
   b. a reflective surface oriented at a skewed angle with respect to the longitudinal axis of said handle; and
   c. a needle holder directly attached to said reflective surface and configured to hold a first end of a needle, said needle holder being positioned and oriented to allow viewing of a second end of the needle in said reflective surface while the first end of the needle is being held in the needle holder as the second end of the needle is passed under the iris and inserted into the tissue of a patient's eye.

2. A mirror according to claim 1 wherein said needle holder comprises a tubular structure.

3. A mirror according to claim 1 wherein said needle holder comprises a tubular structure rigidly affixed to said reflective surface.

4. A mirror according to claim 1 wherein said needle holder comprises a tubular structure welded or soldered directly to said reflective surface.

5. A mirror according to claim 1 wherein said needle holder is positioned and oriented with respect to said reflective surface so that, while the first end of the needle is being held in the needle holder, said reflective surface extends further from a point on said needle holder than the second end of the needle extends from said point.

6. A mirror according to claim 1 wherein said needle holder comprises a length of cannula secured directly to said reflective surface and having a large enough bore to hold the needle therein.

7. A mirror according to claim 1 wherein said reflective surface is carried by said handle.

8. An anterior segment mirror for use in eye surgery, comprising a handle having a reflective-surface at a distal end thereof, said reflective surface extending at an angle to said handle, and a needle holder directly connected to the reflective surface, said needle holder configured and oriented to support a needle and allows for viewing of the passage of the needle under the iris and through the sclera of a patient's eye during the eye surgery.

9. A method of suturing during eye surgery, comprising the steps of:
   a. holding a first end of a needle with a needle holder affixed to a reflective surface of a mirror also having a handle; and
   b. while viewing a second end of the needle in the reflective surface and while holding the handle of the mirror, and inserting the second end of the needle into the tissue of a patient's eye.

10. A method of suturing during eye surgery according to claim 9 wherein said step of inserting the second end of the needle into the tissue of a patient's eye comprises the step of inserting the second end of the needle into the anterior segment of a patient's eye.

11. A method of suturing during eye surgery according to claim 9 wherein said step of inserting the second end of the needle into the tissue of a patient's eye comprises the step of inserting the second end of the needle into the ciliary sulcus of a patient's eye.

12. A method of suturing during eye surgery according to claim 11 further comprising the step of transilluminating through the scleral of the patient's eye to see the ciliary sulcus of the patient's eye.

13. A surgical instrument for use in forming multiple sutures in the ciliary sulcus of a human eye during corneal transplant surgery, the surgical instrument being adapted to releasably hold the base end of a suture needle having suture thread attached thereto so that the needle can be manipulated by the surgical instrument to make multiple passes into the ciliary sulcus for the formation of multiple sutures therein, the surgical instrument further being adapted to allow direct visual viewing of the distal end of the needle while the distal end is passed under the iris and inserted into the ciliary sulcus for placement of suture loops therein, the surgical instrument comprising:
   a. a handle;
   b. a reflective surface oriented at a skewed angle with respect to the longitudinal axis of the handle; and
   c. a needle holder comprising a tubular structure for releasably holding the base end of the suture needle, the bore and ends of the tubular structure being highly polished and smooth, the tubular structure being directly mounted on the reflective surface and positioned so that the distal end of the needle can be viewed in the reflective surface as the distal end is being passed under the iris and inserted into the tissue of a patient's eye.

14. A surgical instrument according to claim 13, wherein said needle holder comprises a tubular structure welded or soldered directly to said reflective surface.

15. A surgical instrument according to claim 13, wherein said needle holder comprises a cannula secured directly to said reflective surface and having a large enough bore to hold the needle therein.

16. A surgical instrument according to claim 13, wherein the distal end of the needle does not extend beyond the edge of the reflective surface when the needle is held in the tubular structure.

17. A surgical instrument according to claim 16, wherein the tubular structure has a trailing end facing the handle and a leading end opposite thereto.

18. A surgical instrument according to claim 17, wherein distance between the opposite end of the tubular structure and the edge of the reflective surface is about 3 mm.

* * * * *